United States Patent
Shin

(10) Patent No.: US 10,203,753 B2
(45) Date of Patent: Feb. 12, 2019

(54) VIDEO IMMERSION INDUCING APPARATUS AND VIDEO IMMERSION INDUCING METHOD USING THE APPARATUS

(71) Applicant: NHN Entertainment Corporation, Seongnam-si (KR)

(72) Inventor: Kyung-Soon Shin, Seongnam-si (KR)

(73) Assignee: NHN Entertainment Corporation, Seongnam-si (KR)

(*) Notice: Subject to any disclaimer, the term of this patent is extended or adjusted under 35 U.S.C. 154(b) by 233 days.

(21) Appl. No.: 14/797,580

(22) Filed: Jul. 13, 2015

(65) Prior Publication Data
US 2016/0011840 A1    Jan. 14, 2016

(30) Foreign Application Priority Data
Jul. 14, 2014  (KR) .......................... 10-2014-0088255

(51) Int. Cl.
| | | |
|---|---|---|
| *G06F 3/01* | (2006.01) | |
| *A61B 5/053* | (2006.01) | |
| *A61B 5/11* | (2006.01) | |
| *A61B 5/16* | (2006.01) | |
| *A61B 5/00* | (2006.01) | |

(52) U.S. Cl.
CPC ............ *G06F 3/013* (2013.01); *A61B 5/0077* (2013.01); *A61B 5/0533* (2013.01); *A61B 5/1114* (2013.01); *A61B 5/168* (2013.01); *A61B 5/7455* (2013.01); *G06F 3/011* (2013.01); *G06F 3/015* (2013.01); *G06F 3/016* (2013.01);
(Continued)

(58) Field of Classification Search
CPC ... A61B 3/113; H04N 5/23229; A61M 21/00; G06F 1/00; G06F 15/28; G06F 17/30; G06F 21/31; A63F 13/06
See application file for complete search history.

(56) References Cited

U.S. PATENT DOCUMENTS

| | | | | |
|---|---|---|---|---|
| 5,016,213 A | * | 5/1991 | Dilts ................... | A61B 5/0533 341/20 |
| 8,708,884 B1 | * | 4/2014 | Smyth .................. | A61M 21/00 600/27 |

(Continued)

FOREIGN PATENT DOCUMENTS

| | | |
|---|---|---|
| JP | 1997277849 | 10/1997 |
| JP | 1998078743 | 3/1998 |

(Continued)

*Primary Examiner* — Lun-Yi Lao
*Assistant Examiner* — Johny Lau
(74) *Attorney, Agent, or Firm* — H.C. Park & Associates, PLC

(57) ABSTRACT

An apparatus for inducing immersion in video and a method for inducing immersion in video is disclosed. The apparatus includes a measuring unit, a control unit and an immersion inducing unit. The measuring unit obtains skin measurement data of a user watching a video output from an image display device and outputs the measured skin measurement data. The control unit outputs an immersion inducing control signal when the measured skin conductivity level is outside of a normal range of skin conductivity values. The immersion inducing unit receives the immersion inducing control signal from the control unit and outputs an immersion inducing message.

17 Claims, 7 Drawing Sheets

(52) U.S. Cl.
CPC ........... *A61B 5/0022* (2013.01); *A61B 5/6898* (2013.01); *A61B 5/742* (2013.01); *A61B 5/7475* (2013.01)

(56) References Cited

U.S. PATENT DOCUMENTS

| | | | |
|---|---|---|---|
| 2008/0081692 A1* | 4/2008 | Pope | A63F 13/06 463/31 |
| 2013/0182144 A1* | 7/2013 | Klinghult | H04N 5/23229 348/231.2 |
| 2015/0135298 A1* | 5/2015 | Robison | G06F 21/31 726/10 |
| 2015/0213019 A1* | 7/2015 | Marvit | G06Q 30/0242 707/748 |
| 2016/0342205 A1* | 11/2016 | Shigeta | A61B 3/113 |

FOREIGN PATENT DOCUMENTS

| | | |
|---|---|---|
| JP | 1999345073 | 12/1999 |
| JP | 2000037364 | 2/2000 |
| JP | 2003248768 | 9/2003 |
| JP | 2005244375 | 9/2005 |
| JP | 2013097311 | 5/2013 |
| JP | 2014-100227 | 6/2014 |
| KR | 10-1042780 | 6/2011 |
| KR | 10-1236139 | 2/2013 |

* cited by examiner

[Figure 1]
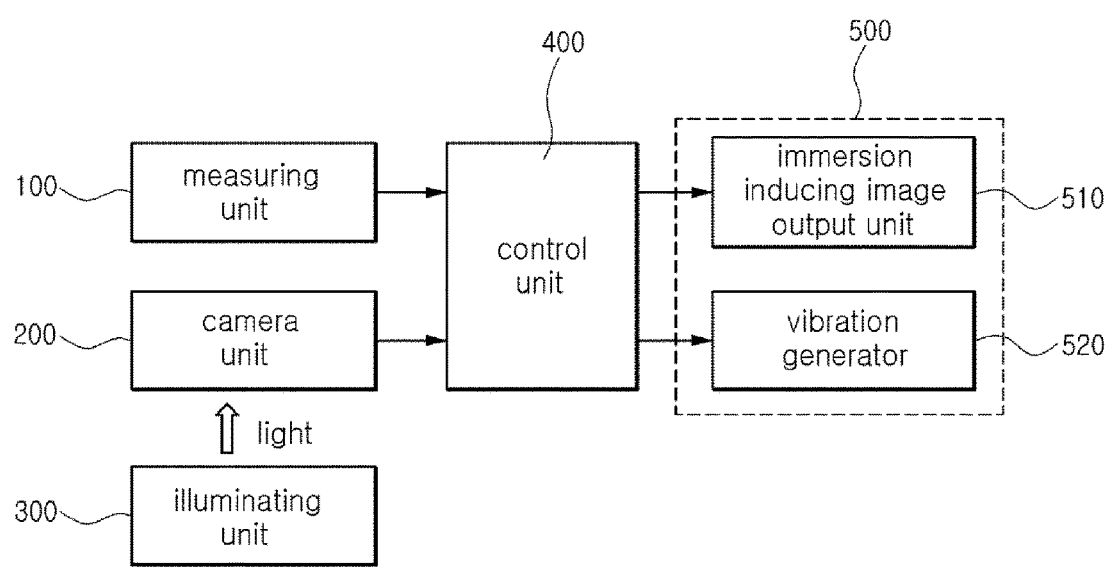

[Figure 2]
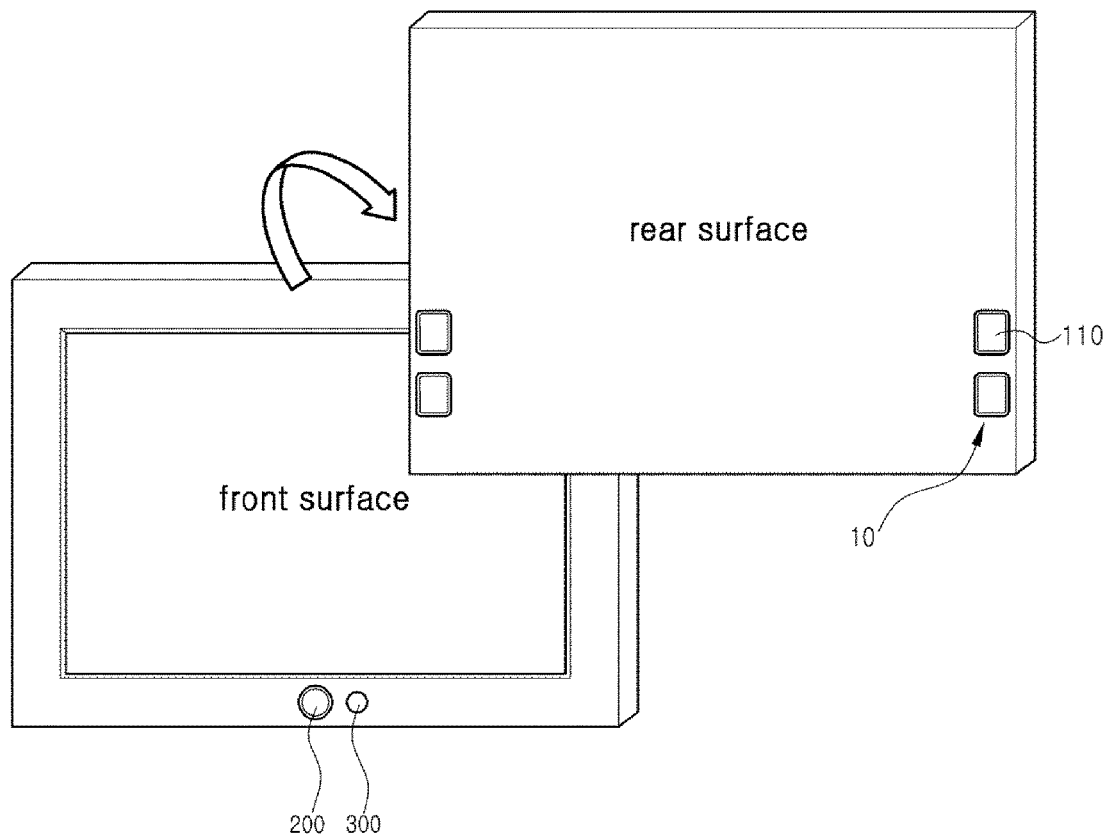

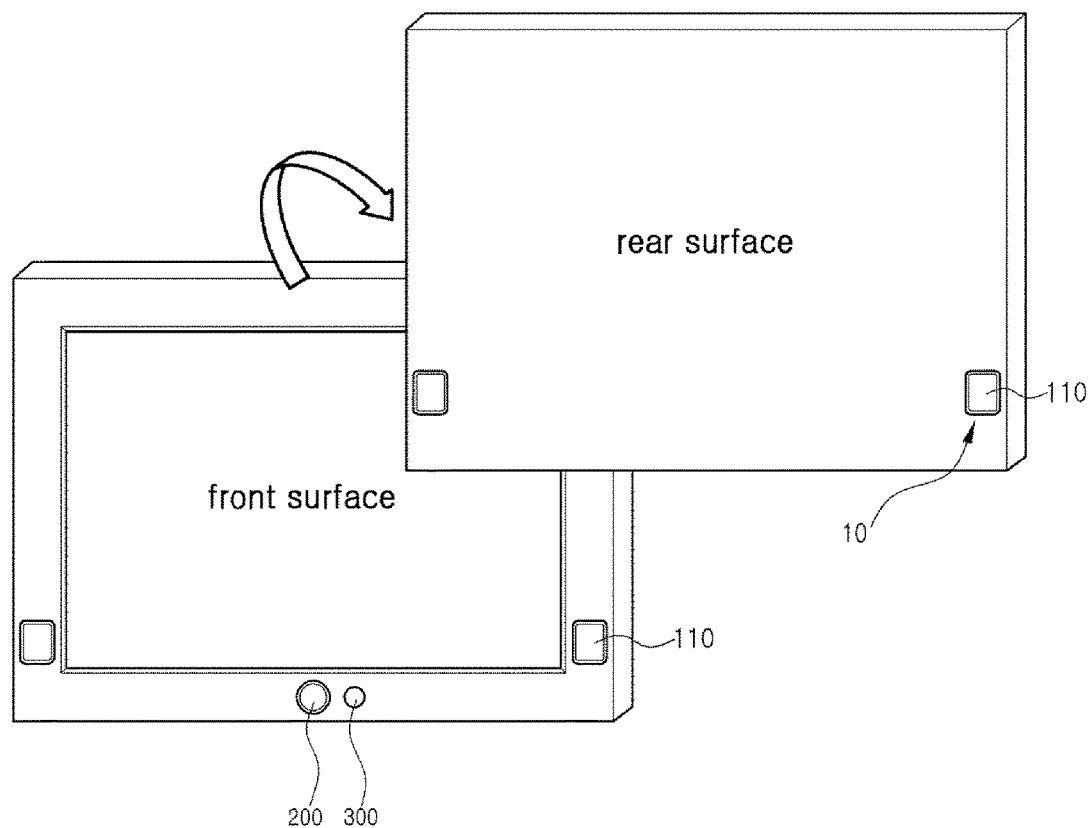

[Figure 4]
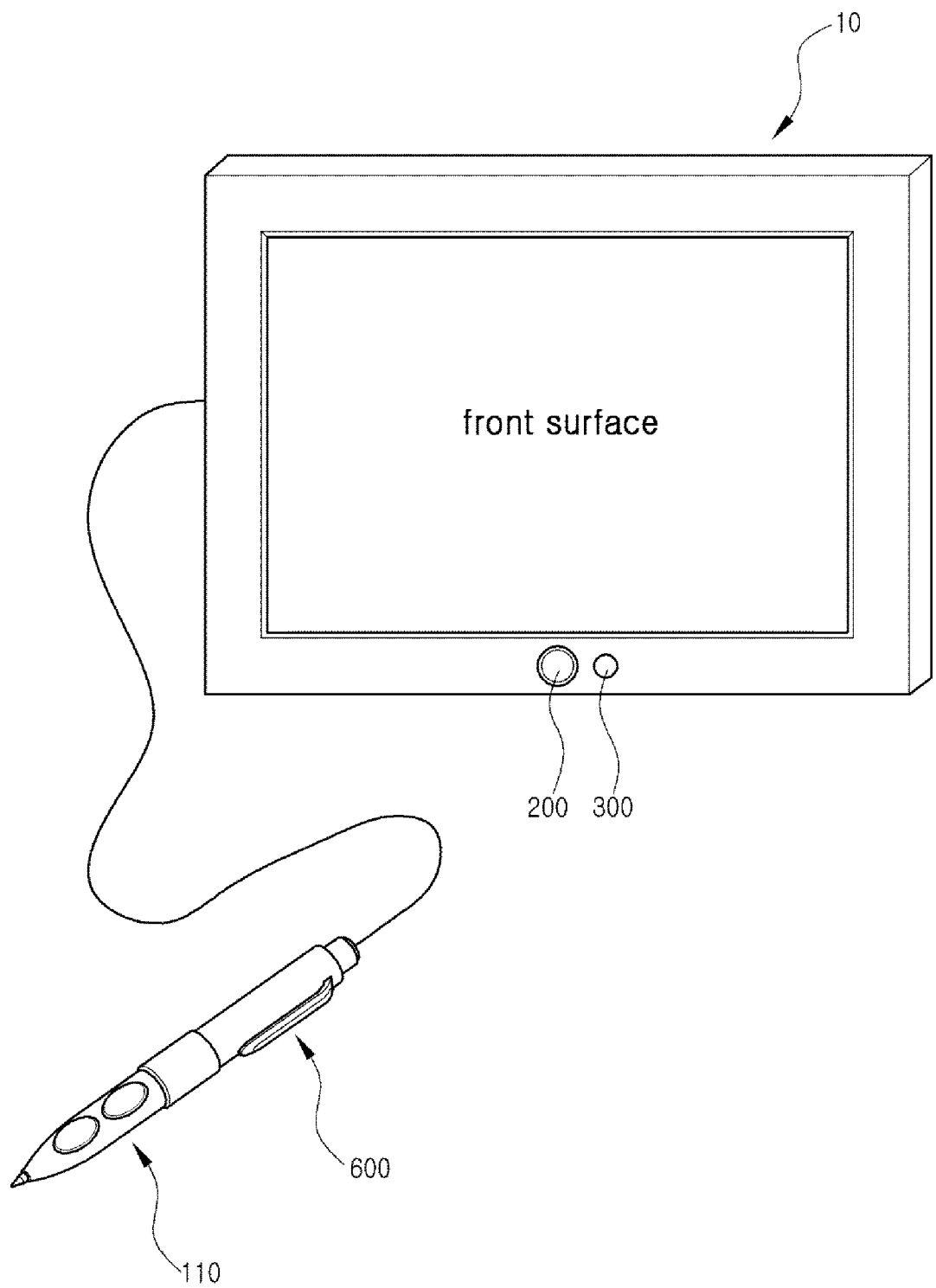

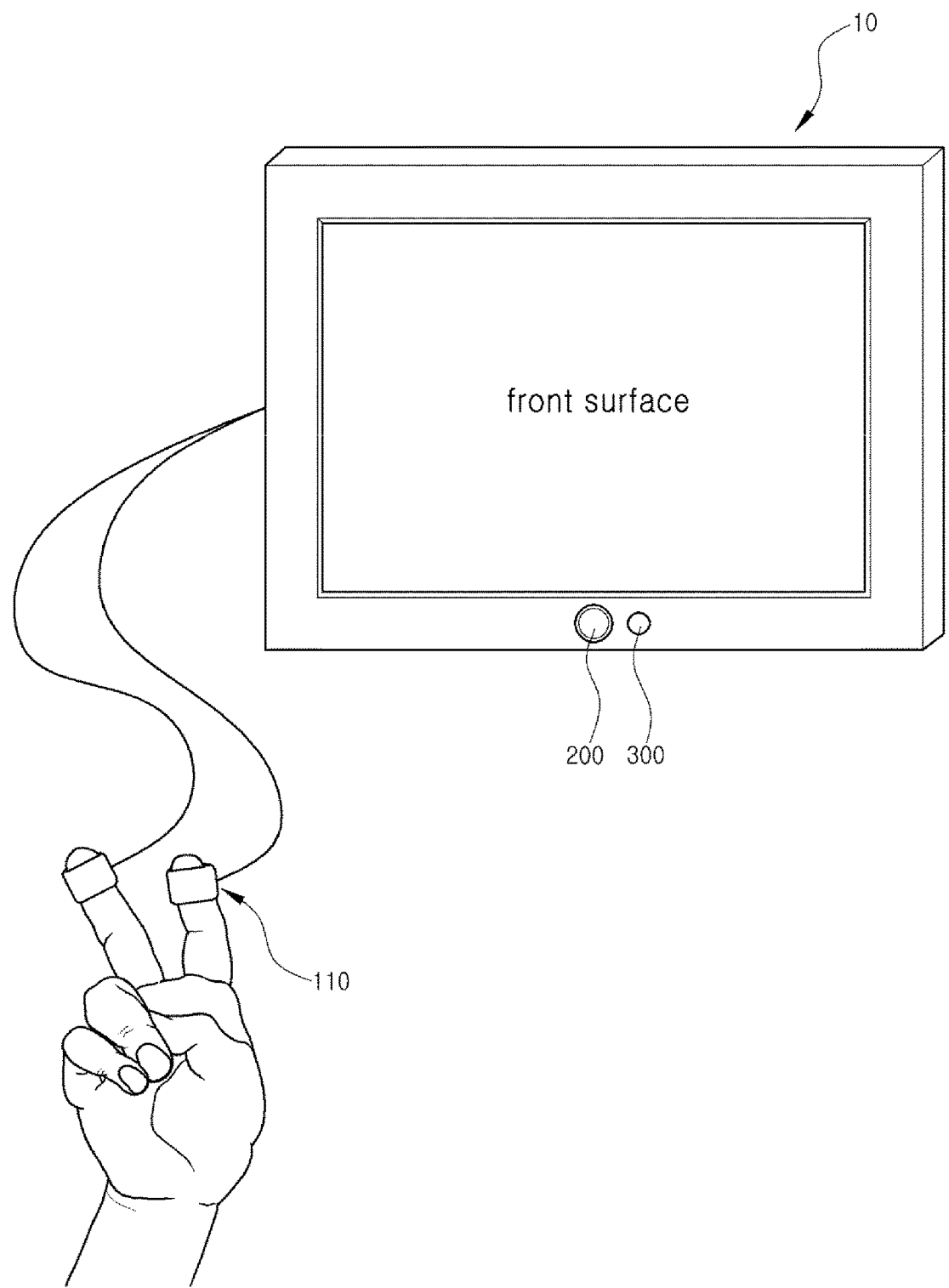
[Figure 5]

[Figure 6]
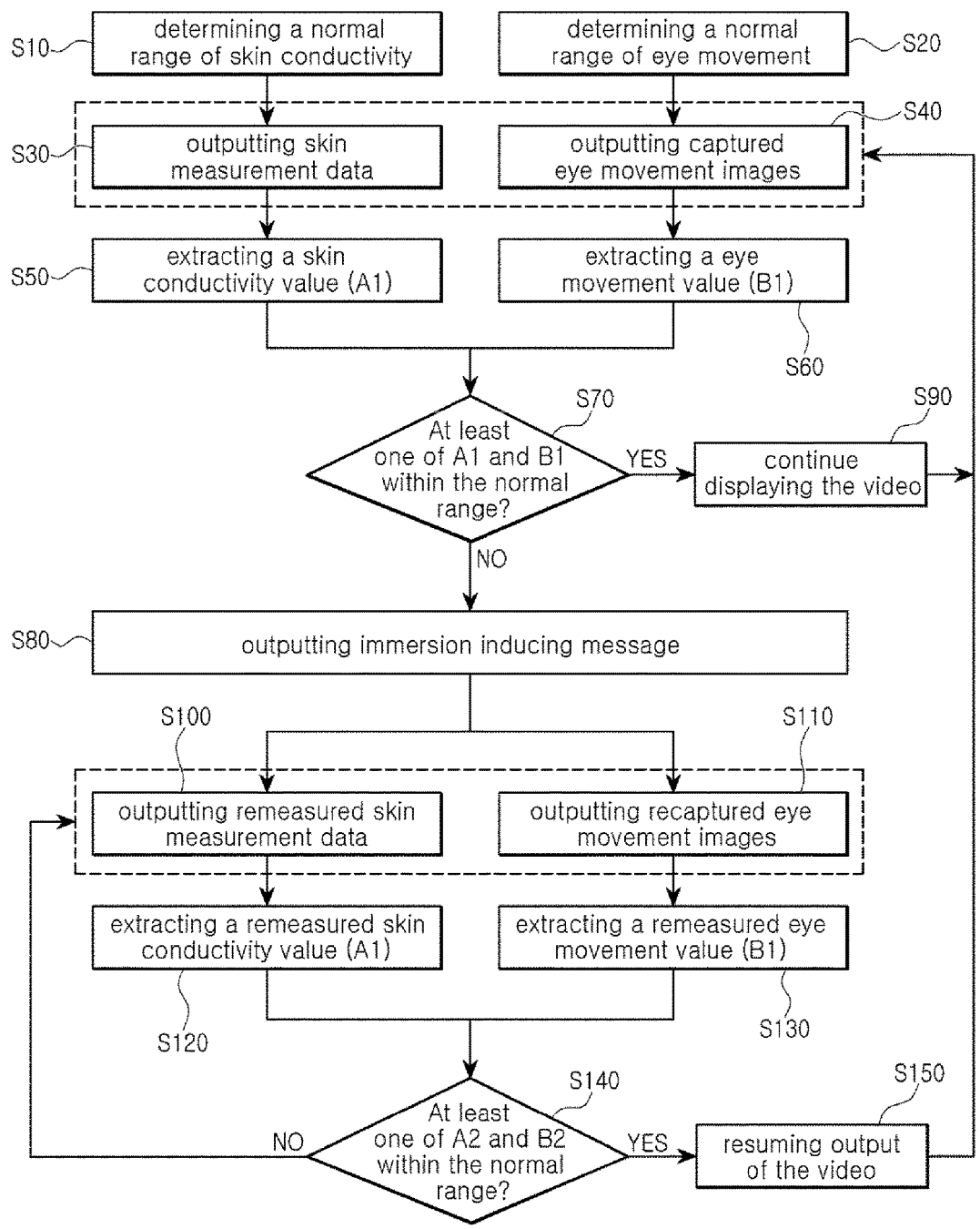

[Figure 7]
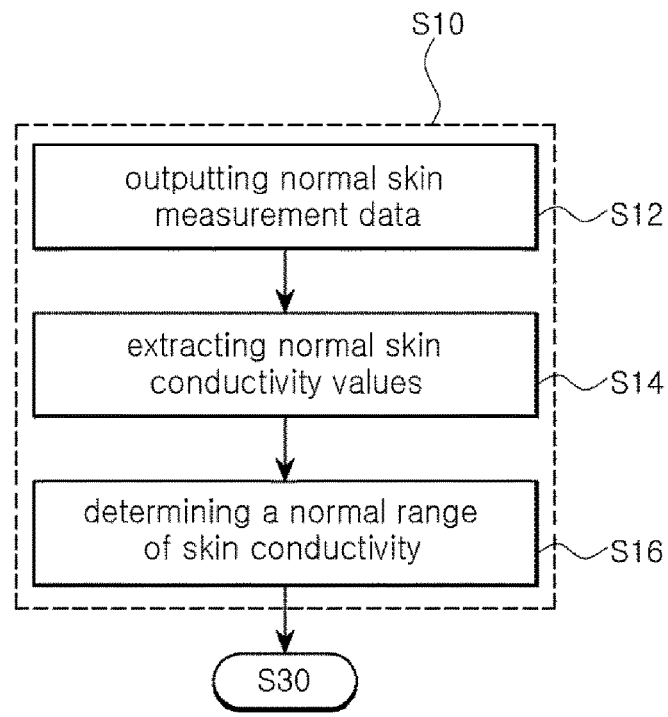
[Figure 8]
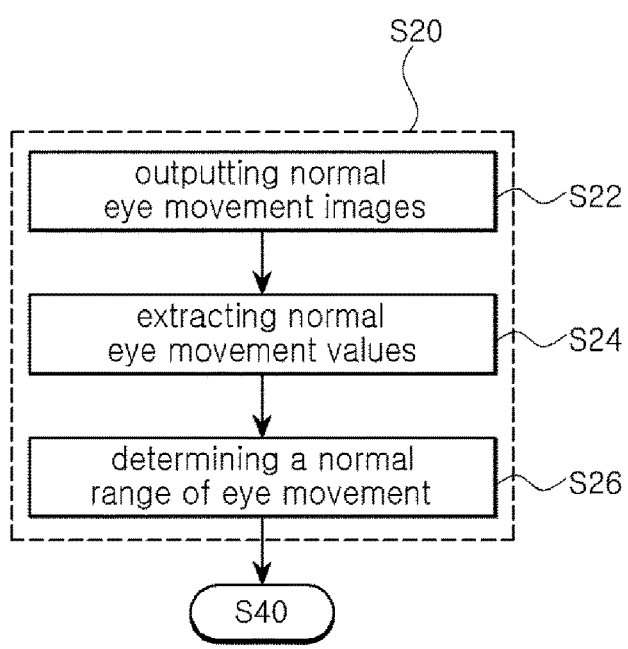

VIDEO IMMERSION INDUCING APPARATUS AND VIDEO IMMERSION INDUCING METHOD USING THE APPARATUS

CROSS REFERENCE TO RELATED APPLICATION

This application claims priority from and the benefit of Korean Patent Application No. 10-2014-0088255, filed on Jul. 14, 2014, which is hereby incorporated by reference for all purposes as if fully set forth herein.

BACKGROUND

Field

Exemplary embodiments relate to an apparatus for inducing a user to be immersed in video and a method for inducing a user to be immersed in video. More particularly, exemplary embodiments relate to an apparatus for inducing immersing a user in online video contents and a method for inducing immersing a user in online video contents using the same.

Discussion of the Background

Development in the internet related technologies have resulted in an increase of data transfer speed allowing people to watch videos anywhere through computers or mobile devices, e.g., smartphone, tablet PC, PDA, etc. For example, in the educational field, any person can watch desired video lectures through mobile devices or computers connected to an internet network without physically attending educational institutions. More specifically, anyone having a device which can access an internet network and play videos may watch video lectures by real-time streaming or by downloading-and-playing, which may save cost and time spent for education.

However, in general, in video lectures because teaching is performed one-way, i.e., without direct interaction between teacher and student, students may find it difficult to be immersed in lectures. Therefore, for a more efficient learning system, proper feedback by students being immersed in the video lectures according to learning process is necessary.

For this purpose, for example, a method of feedback by measuring brainwaves of students has been introduced. However, this feedback method requires complex and inconvenient brainwave measurement equipment and noise-shielding space for eliminating external signals.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide an apparatus and method for inducing a user who is watching videos to be immersed in the videos.

Additional aspects will be set forth in the detailed description which follows, and, in part, will be apparent from the disclosure, or may be learned by practice of the inventive concept.

According to exemplary embodiments, the present invention discloses an apparatus for inducing immersion in videos comprising a measuring unit, a control unit and an immersion inducing unit. The measuring unit obtains skin measurement data of a user watching videos output from an image display device and outputs the measured skin measurement data. The control unit outputs an immersion inducing control signal when the measured skin conductivity level is outside of a normal range of skin conductivity values. The immersion inducing unit receives the immersion inducing control signal from the control unit and outputs an immersion inducing message.

According to an exemplary embodiment of the present invention, the apparatus may include a camera unit capturing eye movement images of the user and outputting the captured eye movement images. The control unit receives the eye movement images from the camera unit, analyzes the eye movement images to calculate eye movement values and determines whether the eye movement is out of a normal range of eye movement values and outputs the immersion inducing control signal when the measured skin conductivity level is out of a normal range of skin conductivity values and the analyzed eye movement is out of the normal range of eye movement values. The eye movement values may include at least one of eye blinking measurement value measured from the user, pupil size measurement value measured from the user, and line of sight of the user.

An exemplary embodiment of the present invention also discloses a method for inducing immersion in videos comprising obtaining, by a measuring unit, skin measurement data of a user watching videos output from an image display device and outputting the obtained skin measurement data, obtaining, by the camera unit, eye movement images of the user, extracting a skin conductivity level from the skin measurement data, analyzing the pictures of the user to extract eye movement of the user, and outputting, by a control unit, an immersion inducing message when the skin conductivity level is out of a normal range of skin conductivity values and the eye movement of the user is out of a normal range of eye movement values.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

FIG. 1 is a block diagram illustrating an apparatus for inducing immersion in videos according to one or more exemplary embodiments.

FIG. 2 illustrates an exemplary embodiment of an image display device including an apparatus for inducing immersion in videos of FIG. 1.

FIG. 3 illustrates an exemplary embodiment of an image display device including an apparatus for inducing immersion in videos of FIG. 1.

FIG. 4 illustrates an exemplary embodiment of an image display device including an apparatus for inducing immersion in videos of FIG. 1.

FIG. 5 illustrates an exemplary embodiment of an image display device including an apparatus for inducing immersion in videos of FIG. 1.

FIG. 6 is a flow chart illustrating a method for inducing immersion in images according to one or more exemplary embodiments.

FIG. 7 is a flow chart illustrating process for determining a normal range of skin conductivity according to one or more exemplary embodiments.

FIG. 8 is a flow chart illustrating process for determining a normal range of eye movement range according to one or more exemplary embodiments.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. As such, the regions illustrated in the drawings are schematic in nature and their shapes are not intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

FIG. 1 is a block diagram illustrating an apparatus for inducing immersion in videos according to one or more exemplary embodiments, and FIG. 2 illustrates an exemplary embodiment of an image display device including an apparatus for inducing immersion in videos of FIG. 1.

Referring to FIG. 1 and FIG. 2, an exemplary embodiment of an apparatus for inducing immersion in videos may be integrated into an image display device 10 and induces a user to be immersed in the videos displayed by the image display device.

The term "videos" may mean not only a plurality of simple images but also motion pictures with audio. Therefore, the image display device 10 may be a display device simply displaying videos or a multimedia device outputting images with audio. The image display device 10 may be, for example, one of a mobile terminal such as a smartphone or tablet PC, computer system such as PC with monitor or laptop computer, and personal multimedia player.

The apparatus for inducing immersion in videos may include a measuring unit 100, camera unit 200, light emitting unit 300, control unit 400, and an immersion inducing unit 500.

The measuring unit 100 is in contact with a user's body to obtain skin measurement data of the user watching videos output from an image display device 10 and outputs the measured skin measurement data. The measuring unit 100 may be integrated into the image display device 10, or may be separated from the image display device 10.

According to an exemplary embodiment, the measuring unit 100 may have at least two sensors 110 to measure skin conductivity of the user.

The control unit 400 outputs an immersion inducing control signal when the measured skin conductivity level is outside of a normal range of skin conductivity values. The immersion inducing unit 500 receives the immersion inducing control signal from the control unit 400 and may output an immersion inducing message.

The skin measurement data may be voltage values measured by the sensors 110. For example, the sensors 110 may measure voltage values at the part in contact with the user's body and transmit the measured voltage values to the control unit 400. Then, the control unit 400 may calculate the skin conductivity using the voltage values.

The skin measurement data may be skin conductivity values which can be used without additional processing, e.g., calculation or referring to look-up table. For example, the measuring unit 100 may include a calculator (not shown) to calculate skin conductivity value based on voltage values measured by the sensors 110. The calculator (not shown) may be integrated into the image display device 10 or may be separately provided.

According to an exemplary embodiment, the sensors 110 may be disposed on an edge or edges of a surface of the image display device 10. For example, two sensors 110 may be disposed on each of two edges, facing each other, of the rear surface, which is a non-display surface, of the image display device 10 as shown FIG. 2. In this case, the sensors 110 can be easily may be in contact with fingers of the user when the user holds the image display device with his or her hands to watch videos because the sensors 110 are disposed on rear surface edges of the image display device 10.

According to an exemplary embodiment, the sensors 110 may be disposed on an edge or edges of a front surface, which is a displaying surface, of the image display device 10. In this case, the user can touch the sensors 110 with a part of body, e.g., fingers, when the user watches videos through the images player device 10 which are laid on for example, desk or cradle. The edge(s) of the image display device 10 may be a bezel of the image display device.

The camera unit 200 may capture the user's eyes to output eye movement images for analyzing eye movement of the user. For example, the camera unit 200 may include a camera capturing the user's eyes. The camera unit 200 may be integrated into the image display device 10, or separated from the image display device 10.

The camera unit 200, for example, may be disposed on an edge of a front surface of the image display device 10. The camera unit 200, therefore, may easily capture eyes of the user watching videos displayed by the image display device 10.

The light emitting unit 300 may provide light for the camera unit 200 to capture the user's eyes. The light emitting unit 300 may be disposed at a position that is appropriate to illuminate the user. For example, the light emitting unit 300 may be disposed adjacent to the camera unit 200 on an edge of a front surface of the image display device 10.

According to an exemplary embodiment, the light emitting unit 300 may include an infrared light source, and the camera unit 200 may have a function of infrared imaging. In this case, the camera unit 200 can capture the user without dazzling the user's eyes because the light emitting unit 300 illuminates the user with infrared light.

The control unit 400 is connected to the measuring unit 100 and the camera unit 200 to receive the skin measurement data and the eye movement images from the measuring unit 100 and the camera unit 200, respectively. The control unit 400 may be connected through wire or wirelessly with the measuring unit 100 and the camera unit 200 to exchange data and signals.

The control unit 400 may extract skin conductivity value from the skin measurement data received from the measuring unit 100. Extracting skin conductivity value from the skin measurement data may be carried out by, for example, calculating skin conductivity value based on the skin measurement data or by directly reading the skin conductivity value from the skin measurement data.

According to the first example, the control unit 400 may calculate the skin conductivity value based on voltage values measured by the sensors 110. The control unit 400, for example, may calculate the skin conductivity value based on voltages measured between two different parts of body by the sensors 110.

According to the second example, the control unit 400 may directly read the skin conductivity value from the skin measurement data received from the measuring unit 100 without calculating process because the skin conductivity value includes skin conductivity value.

The control unit 400 may extract eye movement value by analyzing the eye movement images received from the camera unit 200. It is necessary to extract data only related to eye movement of the user because the eye movement images are simple images of user's eye.

According to an exemplary embodiment, the eye movement value may include at least one of eye blinking frequency of the user, change of pupil size of the user, and direction of sight of the user. The control unit 400 may extract at least one of eye blinking frequency of the user, change of pupil size of the user, and direction of sight of the user, after analyzing the eye movement images.

The control unit 400 may determine whether the skin conductivity value is outside of the normal range of skin conductivity values and whether the eye movement is outside of the normal range of eye movement values. The control unit 400 may output the immersion inducing control signal when both values are outside of predetermined ranges. The normal range of skin conductivity values means a range of skin conductivity measured at a stable state of the user. The normal range of eye movement values means measured at a stable state of the user.

According to an exemplary embodiment, the normal range of eye movement values includes at least one of normal range of eye blinking frequency of the user, normal pupil size of the user, and normal range of direction of sight of the user. Each of normal range is compared to the measured data. The control unit 400 determines whether the eye movement of the user is out of the predetermined range by at least one of comparing the measured eye blinking frequency to the normal eye blink frequency range, comparing the measured pupil size to the normal pupil size range, and comparing the measured direction of sight to the normal range of direction of sight.

The control unit 400 may determine the normal range of skin conductivity values using normal skin conductivity value measured and output by the measuring unit 100. The normal skin measurement data are measured during a stable state of the user. The stable state, for example, includes a state before the user watches the video or after user watches the video.

The control unit 400 may determines the normal range of eye movement values using normal eye movement images captured by the camera unit 200 before or after the user is exposed to the video.

As described above, the control unit 400 sets a normal range of skin conductivity values and a normal range of eye movement values using skin conductivity values and eye movement measured before or after the user is exposed to the video, which allows to personalize a normal range for each person. The control unit 400 can personalize normal ranges for each person considering differences of a stable state between individuals.

Meanwhile, the predetermined ranges of skin conductivity and eye movement may be stored in a memory which may be built in the control unit 400. For example, the predetermined ranges for each person whose normal skin conductivity values and normal eye movement values previously have been measured at a stable state may be stored in a memory. In this case, the control unit 400 may read the stored predetermined ranges from the memory.

Also, the control unit 400 may include a processor which may be built in the image display device 10 to control display of the video, or a processor separate from the image display device 10. The control unit 400 may be electrically connected to the light emitting unit 300 and control the light emitting unit 300.

The immersion inducing unit 500 may receive the immersion inducing control signal from the control unit 400 and output an immersion inducing message according to the immersion inducing control signal. The immersion inducing unit 500 may be connected to the control unit 400 through wire or wirelessly to the control unit 400.

The immersion inducing unit 500 may include an immersion inducing image output unit 510 which outputs immersion inducing images according to an image control signal included in the immersion inducing control signal from the control unit 400. The immersion inducing images may include images and sounds which call the user's attention to the images, or messages which notify the current state of the user.

The immersion inducing image output unit 510 may suspend output of the videos to output the immersion inducing images. In an exemplary embodiment, the immersion inducing image output unit 510 may be an image displaying means which is built in the image display device 10 or be a device separate from the image display device 10.

The immersion inducing unit 500 may include a vibration generator 520 which generates a vibration to call the user's attention according to a vibration generating control signal included in the immersion inducing signal.

The vibration generator 520 may be built in the image display device 10, or may be a device separate from the image display device 10. For example, the vibration generator 520 may be attached to the body of the user. The vibration generator 520 may make the user concentrate his or her attention on the videos more easily by providing the user with vibration.

One or more exemplary embodiments describing where the sensors 110 are attached will be described hereinafter.

FIG. 3 illustrates an exemplary embodiment of an image display device including an apparatus for inducing immersion in videos of FIG. 1.

Referring to FIG. 3, the sensors 110 may be disposed on an edge of a front surface of the image display device 10 and a portion of a rear surface of the image display device 10. The portion of the rear surface corresponds to the edge of the front surface. Therefore, measurement of the skin conductivity through fingers of the user may be performed when the user holds the image display device 10 to watch the videos with his or her fingers.

FIG. 4 illustrates an exemplary embodiment of an image display device including an apparatus for inducing immersion in videos of FIG. 1.

Referring to FIG. 4, the sensors 110 may be disposed on an auxiliary device 600 which is separated from the image display device 10. The auxiliary device 600 may be a device wearable or usable for the user, e.g., a watch, eyeglasses, an earphone, a headphone, a pen, or mouse. In the FIG. 4, a pen is illustrated as an example of the auxiliary device 600, but aspects of the invention are not limited thereto.

FIG. 5 illustrates an exemplary embodiment of an image display device including an apparatus for inducing immersion in videos of FIG. 1

Referring to FIG. 5, the sensors 110 may be directly attached to a part of the user's body using attaching means, e.g., tape, band, clip, etc. The part of the user's body may be, e.g., finger(s), palm(s), toe(s) or sole(s) of the user. FIG. 5 depicts fingers of the user as an example, but aspects of the invention are not limited thereto.

As described above, measurement of the skin conductivity can be performed through the auxiliary device 600 or attaching means.

While the immersion inducing messages or images are provided when both of the skin conductivity value and eye movement are outside of normal ranges in the above, the immersion inducing messages or images may be provided when either the skin conductivity value or eye movement is outside of normal ranges in the above The method for inducing immersion in video using the immersion inducing apparatus described above will be described hereinafter.

FIG. 6 is a flow chart illustrating a method for inducing immersion in videos according to an exemplary embodiment of the present invention, FIG. 7 is a flow chart illustrating process for determining normal range of skin conductivity value, and FIG. 8 is a flow chart illustrating process for determining normal range of eye movement values.

Referring to FIG. 6, FIG. 7, and FIG. 8, the steps of determining a normal range of skin conductivity values S10, and determining a normal range of eye movement values S20 may be performed independently.

In the step of determining a normal range of skin conductivity values in step S10, the measuring unit 100 measures and outputs normal skin measurement data at a stable state of the user in step S12. Then, the control unit 400 extracts normal skin conductivity values from the skin measurement data in step S14. Subsequently, the control unit 400 determines a normal range of skin conductivity values in step S16 using the normal skin conductivity values.

In the step of determining a normal range of eye movement values in step S20, the camera unit 200 captures the user's eyes to output normal eye movement images at a stable state of the user in step S22. Then, the control unit 400 analyzes the captured normal eye movement images and extracts normal eye movement values in step S24. Subsequently, the control unit 400 determines the normal range of eye movement values using the normal eye movement values in step S26.

The measuring unit 100 then measures the skin conductivity of the user when the user is watching the videos and outputs the skin measurement data in step S30. The camera unit 200 captures the eye movement of the user and outputs the eye movement images when the user is watching the videos and outputs the skin measurement data in step S40. Steps of S30 and S40 may be performed independently from each other.

Next, the control unit 400 extracts the skin conductivity values A1 from the skin measurement data in step S50, and analyzes the eye movement images to extract the eye movement values B1 in step S60. Steps of S50 and S60 may be performed independently from each other.

Then, the control unit 400 determines whether the skin conductivity values A1 are within the normal range of skin conductivity values and whether the eye movement values B1 are within the normal range of eye movement values in step S70.

When the result of determination of step S70 indicates that the skin conductivity value A1 is outside of the normal range of skin conductivity values and the eye movement value B1 is outside of the normal range of eye movement values, the immersion inducing unit 500 may output the immersion inducing message in step S80. For example, in step S80, the image display device 10 may suspend output of the videos and output the immersion inducing images.

When the result of determination of step S70 indicates that the skin conductivity values A1 are within the normal range of skin conductivity values or the eye movement values B1 are within the normal range of eye movement values, the image display device 10 may continue to output the videos in step S90. Steps of S30 to S70 may be repeatedly performed.

Even when output of the videos is suspended after step S80, the measuring unit 100 may continuously measure the skin conductivity of the user and output re-measured skin conductivity values in step S100. The camera unit 200 may continuously capture the eye movement of the user and output recaptured eye movement images in step S110. Steps of S100 and S110 may be performed independently from each other.

Subsequently, the control unit 400 may extract a re-measured skin conductivity value A2 from the re-measured skin measurement data in step S120 and may extract a re-measured eye movement value B2 from the recaptured eye movement images in step S130. Steps S120 and S130 may be performed independently each other.

The control unit 400 determines whether the re-measured skin conductivity values A2 are within the normal range of skin conductivity values and whether the re-measured eye movement values B2 are within the normal range of eye movement values in step S140.

When the result of determination of step S140 indicates that the re-measured skin conductivity value A2 is within the normal range of skin conductivity values or the re-measured eye movement value B2 is within the normal range of eye movement values, the image display device 10 may resume outputting the videos in step S150. After step S150, steps S40 to S70 may be repeatedly performed.

When the result of determination of step S140 indicates that the re-measured skin conductivity value A2 is outside of the normal range of skin conductivity values and the re-measured eye movement value B2 is outside of the normal range of eye movement values, steps of S100 to S140 may be repeatedly performed.

As described above, resuming output of the suspended videos can be determined by continuously measuring the re-measured skin conductivity value A2 and re-measured eye movement value B2.

As described in detail above, the exemplary embodiments of the present invention provide an apparatus and method for inducing immersion in videos that allows more precise measurement of the user's immersion in the videos displayed by the image display device 10. The apparatus and method may suspend output of the videos and output the immersion inducing videos, which can effectively induce the user to be immersed in the videos again.

The apparatus and method can measure the skin conductivity relatively easily and naturally because the measuring unit 100 may be constructed in various forms and disposed on various parts of the user's body using various attaching means.

Additionally, the apparatus and method may allow the image display device 10 to resume output of the suspended videos by continuously re-measuring the skin conductivity and eye movement of the user after suspending output of the videos.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. An apparatus for inducing a user's immersion in a video comprising:
   a measuring unit configured to obtain skin measurement data of the user watching the video output from an image display device and output the obtained skin measurement data representing the user's immersion in the videos displayed by the image display device;
   a camera unit configured to capture eye movement images of the user and output the captured eye movement images,
   a control unit configured to extract a skin conductivity value from the skin measurement data
   and wherein the control unit receives the eye movement images from the camera unit, analyzes the eye movement images to determine whether the eye movement is outside of a normal range of eye movement values and
   and output an immersion inducing control signal in response to the measured skin conductivity value being outside of a normal range of skin conductivity values and the analyzed eye movement being outside of the normal range of eye movement values; and
   an immersion inducing unit configured to receive the immersion inducing control signal from the control unit and induce the user's immersion in the videos displayed by the image display device by suspending output of the videos and outputting an immersion inducing image in response to the immersion inducing control signal,
   wherein the control unit is configured to resume output of the videos suspended by the immersion inducing unit in response to determining that the skin conductivity value returning to the normal range of skin conductivity values and the eye movement of the user returning to the normal range of eye movement values.

2. The apparatus of claim 1, wherein the control unit determines the normal range of skin conductivity values using a normal skin conductivity value,
   wherein the normal skin conductivity value is measured by the measuring unit in response to the user being at a steady state.

3. The apparatus of claim 2, wherein the steady state of a user is before or after the user watches the video output from the image display device.

4. The apparatus of claim 1, wherein the control unit determines the normal range of eye movement values using a normal eye movement images obtained by the camera unit.

5. The apparatus of claim 4, wherein the eye movement values comprise at least one of eye blinking frequency value measured from the user, pupil size value measured from the user, and direction of sight of the user.

6. The apparatus of claim 1, wherein the camera unit is built in the image display device.

7. The apparatus of claim 6, further comprising a light emitting unit configured to provide light for the camera, wherein the light emitting unit is built in the image display device.

8. The apparatus of claim 6, wherein the light emitting unit comprises an infrared light source.

9. The apparatus of claim 1, wherein the control unit comprises an immersion inducing image output unit configured to output immersion inducing images in response to the immersion inducing control signal.

10. The apparatus of claim 1, wherein the measuring unit comprises at least two sensors in contact with at least two parts of a body of the user.

11. The apparatus of claim 10,
wherein the skin measurement data comprises voltage values measured by the sensors,
wherein the control unit calculates the skin conductivity value using the voltage values.

12. The apparatus of claim 10,
wherein the sensors are disposed on an edge of a front surface of the image display device and a portion of a rear surface of the image display device,
wherein the front surface of the image display device is a displaying surface and the portion of the rear surface corresponds the edge of the front surface.

13. A method for inducing a user's immersion in a video, the method comprising:
obtaining, by a measuring unit, skin measurement data of the user watching the video output from an image display device and outputting the obtained skin measurement data representing the user's immersion in the videos displayed by the image display device;
obtaining, by a camera unit,
capture eye movement images of the user and output the captured eye movement images;
extracting a skin conductivity value from the skin measurement data;
analyzing the eye movement images of the user to extract eye movement of the user;
a control unit analyzing the eye movement images to determine whether the eye movement is outside of a normal range of eye movement values;
outputting an immersion inducing control signal in response to the measured skin conductivity value being outside of a normal range of skin conductivity values and the eye movement of the user is outside of a normal range of eye movement values;
inducing, by an immersion inducing unit, the user's immersion in the videos displayed by the image display device by suspending output of the videos and outputting an immersion inducing image in response to the immersion inducing control signal; and
resuming, by the control unit, output of the videos suspended by the immersion inducing unit in response to determining that the skin conductivity value and the eye movement of the user returning to the normal range of skin conductivity values and the normal range of eye movement values.

14. The method of claim 13, further comprising steps of:
determining the normal range of skin conductivity values; and
determining the normal range of eye movement values.

15. The method of claim 14, wherein the step of determining the normal range of skin conductivity values comprises:
obtaining, by the measuring unit, normal skin measurement data of the user;
extracting a normal skin conductivity value from the normal skin measurement data; and
determining the normal range of skin conductivity values using the normal skin measurement data.

16. The method of claim 14, wherein the step of determining the normal range of eye movement values comprise:
capturing, by the camera unit, normal eye movement images of the user;
analyzing the normal eye movement images of the user to extract normal eye movement of the user; and
determining the normal range of eye movement values using the normal eye movement of the user.

17. The method of claim 13, wherein the resuming of the output of the videos suspended by the immersion inducing unit comprises:
obtaining a remeasured skin measurement data remeasured by the measuring unit after output of the video is suspended;
recapturing eye movement images of the user by the camera unit after output of the video is suspended;
extracting a remeasured skin conductivity level from the remeasured skin measurement data;
analyzing the recaptured eye movement images of the user to extract eye movement value of the user; and
resuming output, by a control unit, of the videos in response to the remeasured skin conductivity level being within the normal range of skin conductivity values and the recaptured eye movement of the user being within the normal range of eye movement values.

\* \* \* \* \*